United States Patent [19] [11] 4,314,026
Descamps-Latscha [45] Feb. 2, 1982

[54] PROCESS FOR DETERMINING THE COMPLEMENT-DEPENDENT CYTOTOXICITY MEDIATED BY ANTI-HLA ANTIBODIES BY MEANS OF ATP DETERMINATION AND DEVICE FOR ATP DETERMINATION

[75] Inventor: Beatrice Descamps-Latscha, Paris, France

[73] Assignee: Institut National de La Sante et de La Recherche Medicale, Paris, France

[21] Appl. No.: 136,056

[22] Filed: Mar. 31, 1980

[51] Int. Cl.³ .................... C12Q 1/66; G01N 33/54
[52] U.S. Cl. ..................................... 435/7; 435/8; 435/291; 23/230 B; 424/8; 424/12; 422/52
[58] Field of Search .............. 435/7, 8, 291, 808; 23/230 B; 424/1.5, 8, 12; 422/52

[56] References Cited

U.S. PATENT DOCUMENTS

| | | | |
|---|---|---|---|
| 3,359,973 | 12/1967 | Hoffman | 435/8 |
| 3,520,660 | 7/1970 | Webb | 435/8 |
| 3,728,227 | 4/1973 | Elson et al. | 435/291 |
| 3,999,948 | 12/1976 | Derndoerfer et al. | 435/7 |
| 4,104,126 | 8/1978 | Young | 435/8 |

FOREIGN PATENT DOCUMENTS 2823916 12/1978 Fed. Rep. of Germany .......... 435/8

OTHER PUBLICATIONS

Descamps, "Determination of Intracellular Adenosinetriphosphate for Detecting Anti-HLA Antibody Medicated Cytolysis, Introduction to a New Method for HLA Typing", Chem. Abstracts, vol. 92, No. 1, p. 294 (1980), Abs. No. 177041q.
Demetriou, et al., "An Enzymatic Method Permitting Early Determination of Histocompatibility in Mixed Lymphocyte Culture", Chem. Abstracts, vol. 90, No. 15, p. 469 (1979), Abs. No. 119497r.
Descamps, Ann. Immunol., (Institut Pasteur), vol. 130, (1979), pp. 595–600.

Primary Examiner—Thomas Wiseman
Attorney, Agent, or Firm—Oblon, Fisher, Spivak, McClelland & Maier

[57] ABSTRACT

The present invention relates to a process for determining the complement-dependent cytotoxicity mediated by anti-HLA antibodies wherein the cytotoxicity is determined by measuring the loss of intracellular ATP after addition of complement to anti-HLA coated target cells.

7 Claims, 7 Drawing Figures

|   | A | B | C | D | E | F |
|---|---|---|---|---|---|---|
| 1 | HLA A1<br>0%<br>– | HLA A1<br>11%<br>– | HLA A1<br>0%<br>– | HLA A9<br>47%<br>++++ | HLA A9<br>10%<br>++ * | AB SERUM<br>–  |
| 2 | HLA A2<br>16%<br>– | HLA A2<br>0%<br>– | HLA A28<br>0%<br>– | HLA A28<br>1%<br>– | HLA A3<br>47%<br>++++ | HLA A3<br>37%<br>++++ |
| 3 | HLA A10<br>11%<br>– | HLA AW25<br>0%<br>– | HLA AW26<br>0%<br>– | HLA A11<br>0%<br>– | HLA A11<br>20%<br>– | HLA A3A11<br>49%<br>++++ |
| 4 | HLA A10<br>0%<br>– | HLA AW32<br>0%<br>– | HLA AW32<br>11%<br>– | HLA A29<br>0%<br>– | HLA A29<br>0%<br>– | HLA A29W33<br>* 58% |
| 5 | HLA B51,52,53<br>12%<br>– | HLA B51,52<br>0%<br>– | HLA B51,52,53<br>0%<br>– | HLA BW16,18<br>37%<br>++++ | HLA BW21<br>0%<br>– | W19<br>14% |
| 6 | HLA BW35,51<br>4%<br>– | HLA BW35,5<br>0%<br>– | HLA BW15<br>0%<br>– | HLA BW15<br>3%<br>– | HLA B17<br>*69%<br>– | HLA B17<br>15%<br>– |
| 7 | HLA B18<br>23%<br>++++ | HLA B18<br>70%<br>++++ | HLA B?40<br>10%<br>– | HLA B40<br>0%<br>– | HLA B27<br>0%<br>– | HLA B27<br>0%<br>– |
| 8 | HLA B7<br>0%<br>– | HLA B7<br>4%<br>– | HLA A26<br>0%<br>– | HLA BW35<br>9%<br>– | HLA BW22<br>0%<br>– | HLA BW22<br>0%<br>– |
| 9 | HLA B8<br>0%<br>– | HLA B8<br>0%<br>– | HLA B14<br>0%<br>– | HLA B14<br>3%<br>– | HLA BW39<br>0%<br>– | HLA BW22<br>6%<br>– |
| 10 | HLA B12<br>76%<br>++++ | HLA B12<br>72%<br>++++ | HLA B13<br>0%<br>– | HLA B13<br>15%<br>– | HLA BW37<br>0%<br>– | HLA B13,40<br>4%<br>– |

HLA typing (MCT) = HLA A3, Aw24; B12, B18

FIG. 6

PROCESS FOR DETERMINING THE COMPLEMENT-DEPENDENT CYTOTOXICITY MEDIATED BY ANTI-HLA ANTIBODIES BY MEANS OF ATP DETERMINATION AND DEVICE FOR ATP DETERMINATION

BACKGROUND OF THE INVENTION

The present invention relates to a process for measuring complement-dependent cytotoxicity mediated by anti-HLA antibodies by means of intracellular ATP loss determination.

The process of the invention is suitable for HLA typing of human lymphoid cells. It is also appropriate for anti-HLA antibodies detection in the serum from subjects sensitized against histocompatibility antigens(-polytransfused patients, multiparous women, organ graft recipients).

One of the main advantages of the invention process is that it can be entirely performed automatically.

PRIOR ART

Numerous methods have been already proposed for detection of HLA antibodies. Among these methods, techniques measuring the release of radioisotopes, such as $^{51}Cr$ from labelled target cells [see SANDERSON AR; Immunology, 1965, 9, 287 and WIGZELL H., Transplantation 1965,3: 423] or of fluorescent compounds [ROTMAN B., Papermaster BW; Proc. Nat. Acad. Sci, 1966, 56, 476] have a high degree of accuracy. Unfortunately, they require too large a number of cells and serum and are too time consuming to be considered for routine or emergency HLA typing.

However, the most frequently used method for determination of complement-dependent cytotoxicity mediated by anti-HLA antibodies is the microcytotoxicity test (currently designated by the abbreviation MCT) which was first proposed by MITTAL et al [Transplantation, 1968,6: 913]. This method, which consists in measuring the uptake of supravital dyes by lysed target cells, has been found to be the most simple, reliable and accurate method for performing routine HLA typing or cross-match test and has been universally accepted by most histocompatibility laboratories. These laboratories have standardized the originally described process with only minor changes from one to another. A recent complete and critical review of the MCT method was published by TERASAKI et al [Ann. J. Clin. Path. 1978,69, 103].

Most of the successive technical steps in the MCT process have now been automatised with the exception of the final step which consists in the reading of the percentage of dead cells. Since this reading should be performed under microscope, it depends on the use of the technician to appreciate the uptake of the supravital dyes and consequently could not be automatised. In addition, this MCT process is often considered to be inadequate for precisely measuring the extent of cell damage. Thus, for these two reasons, it could be of a great interest for histocompatibility centers, to dispose of a more precise and easily quantifiable method for measuring anti-HLA mediated complement-dependent cytotoxicity. Many attempts have been made in order to find such a method.

It was now found a process for measuring cytolysis which is rapid, extremely sensitive and may be entirely automatised.

According to its broadest aspect, the present invention relates to a process for determining complement-dependent cytotoxicity, mediated by anti-HLA antibodies, said process consists in measuring the loss of intracellular ATP after addition of complement to anti-HLA-coated target cells.

In the present specification, the term "ATP" means "adenosine-triphosphate" and "HLA" designates the major histocompatibility system in the human. This abbreviation was initially used for designating "human leucocytes locus A antigens", which were discovered by Jean DAUSSET [Vox Sang(Basel),6,190(1954)]. Now it is still employed, although two groups of loci have been individualized within this same chromosomic region: the first group incluses 3 sub-loci called A, B, C the second, one locus called D [Bach F. H., Van Rood JJ New Engl. J. Med. (1976),295,806-872 and 927].

Adenosine triphosphate ATP is well known as a key substance in the energy metabolism of both microbial and somatic living cells. It plays a major role in metabolic regulation, as proven by its rapid disappearance upon cell death and its complete absence from non-living detrital material and particulate matter. Its concentration is fairly uniform in living cells but rapid fluctuations may occur with changes in environmental conditions or nutritional deficiency. This, however, does not affect the reliability of ATP determination, as demonstrated by its large-scale use in ecological studies. Reference may be made for example to studies of HOLM-HANSEN O [Bull. Ecol. Res. Comm. Stockholm 1973, 17, 215]. In addition, ATP determination is based on a highly sensitive technique, resulting from the demonstration that luminescence in fire flies (Photinus pyralis) requires ATP and cannot use other sources of energy [see HASTING JW, Ann. Rev. Biochem; 1968 37, 603]. More precisely, light production with firefly lantern extract appeared to be strictly proportional to the amount of ATP and to depend on the presence of luciferin-luciferase, oxygen and magnesium ions [see above mentioned studies of HASTING JW and the ones of Mac Elroy WD, Proc. Nath. Acad. Sci. USA, 1974, 33, 342]. Under optimal conditions, each molecule of reacting ATP produces one photon. By means of present ultrasensitive photometers this firefly bioluminescent reaction has now become the most sensitive method for ATP measurement.

To the applicant knowledge, only a few studies have been reported using ATP determination for measuring cytolysis in immunological systems. NUNGESTER et al [Proc. Soc. Exp. Biol. Med. 132, 582 (1969)] reported that measurement of ATP could be suitable technique for revealing cytolysis induced by xenogenic antigens using tumoral mice as target cells. HENNEY CS [J. Immunol. 1973 110,73] used the same indicator to reveal the lymphocytemediated cytotoxicity in mice sensibilized towards tumoral cells. In a recent study performed in mice [Ann. Immunol. (Institut Pasteur), 1979, 130 (595–600)] the applicant showed for the first time that the measurement of ATP could be used for evaluating complement-dependent cytotoxicity mediated by anti-$H_2$ sera.

However, up to now it has never been proposed to use the ATP measurement for detecting in humans HLA antigens or anti-HLA antibodies.

BRIEF DESCRIPTION OF THE INVENTION

The present invention provides an extremely sensitive procedure for measuring complement-dependent cytotoxicity (CDC) mediated by anti-HLA antibodies which presents substantial advantages over the MCT.

According to the process of the invention cytolysis is determined by measuring the intracellular ATP content of human lymphoid cells (target cells) after these latter have been incubated with antiserum (anti HLA antibody) and complement (rabbit serum).

When both target cells and serum share the same HLA specificities, cell lysis is observed and exteriorised by a dramatic loss of its intracellular ATP content.

Tests, which will be hereinafter related, show that the process of the invention is a reliable, reproducible and rapid method, which can be completely automatised and requires minute amounts of cells, serum and complement.

BRIEF DESCRIPTION OF THE DRAWINGS

FIG. 2 to FIG. 7 relate to the data of experiments of following examples:

FIG. 2 shows a correlation between ATP concentration ($x10^{-2}g$) versus light intensity (RLU);

FIG. 3 is a diagram of ATP cell content versus cell number in human peripheral blood lymphocytes (PBL);

FIG. 4 is the target cell HLA specificities and antiserum HLA specificities of cells and sera used in example 2;

FIG. 5 is a diagram of % ATP loss after addition of complement to antibody-coated-target cells (as obtained in example 3);

FIG. 6 is the pattern of serum destribution in microtiter plates used for the assays related in example 4;

FIG. 7 is a comparison between micro ATP-CDC technique of the invention and MCT in 270 serum target combinations.

DETAILED DESCRIPTION OF THE INVENTION

As above indicated the CDC method of the invention consists in determining the cytotoxicity by measuring loss of intracellular ATP after addition of complement to anti-HLA coated target cells.

The preparation of anti-HLA coated target cells and the addition of the complement thereto are carried out according to conventional means, advantageously according to the same micromethodology as the one presently used in MCT for HLA typing as disclosed by TERASAKI et al [Ann. J. Clin. Path, 1978, 69, 103] and will be briefly disclosed hereinafter. These steps may also be carried out by macromethodology, but in this case it is necessary to centrifuge the sample before proceeding to the ATP measurement, as it will be illustrated hereinafter.

First, the target cells are incubated with serum at about 37° C. for about 15 minutes. Thereafter complement is added to serum coated target cells and incubation is continued again at 37° C. for about 5 minutes.

Then, according to the invention process, ATP loss from target cells is measured by any means appropriate for estimating such a loss. For example, this measurement is advantageously performed by bioluminescence, using an enzyme-substrate mixture specific to ATP, such as for example luciferin-luciferase mixture.

The ATP loss measurement by bioluminescence is the preferred embodiment of the invention process and will be hereinafter described, without restricting the scope of the invention to this preferred embodiment.

According to this preferred embodiment the ATP loss measurement is carried out as follows:

(1) ATP is extracted from the cells by an appropriate reagent, (2) the specific enzyme-substrate mixture is added and (3) bioluminescence is measured.

Figure 1:
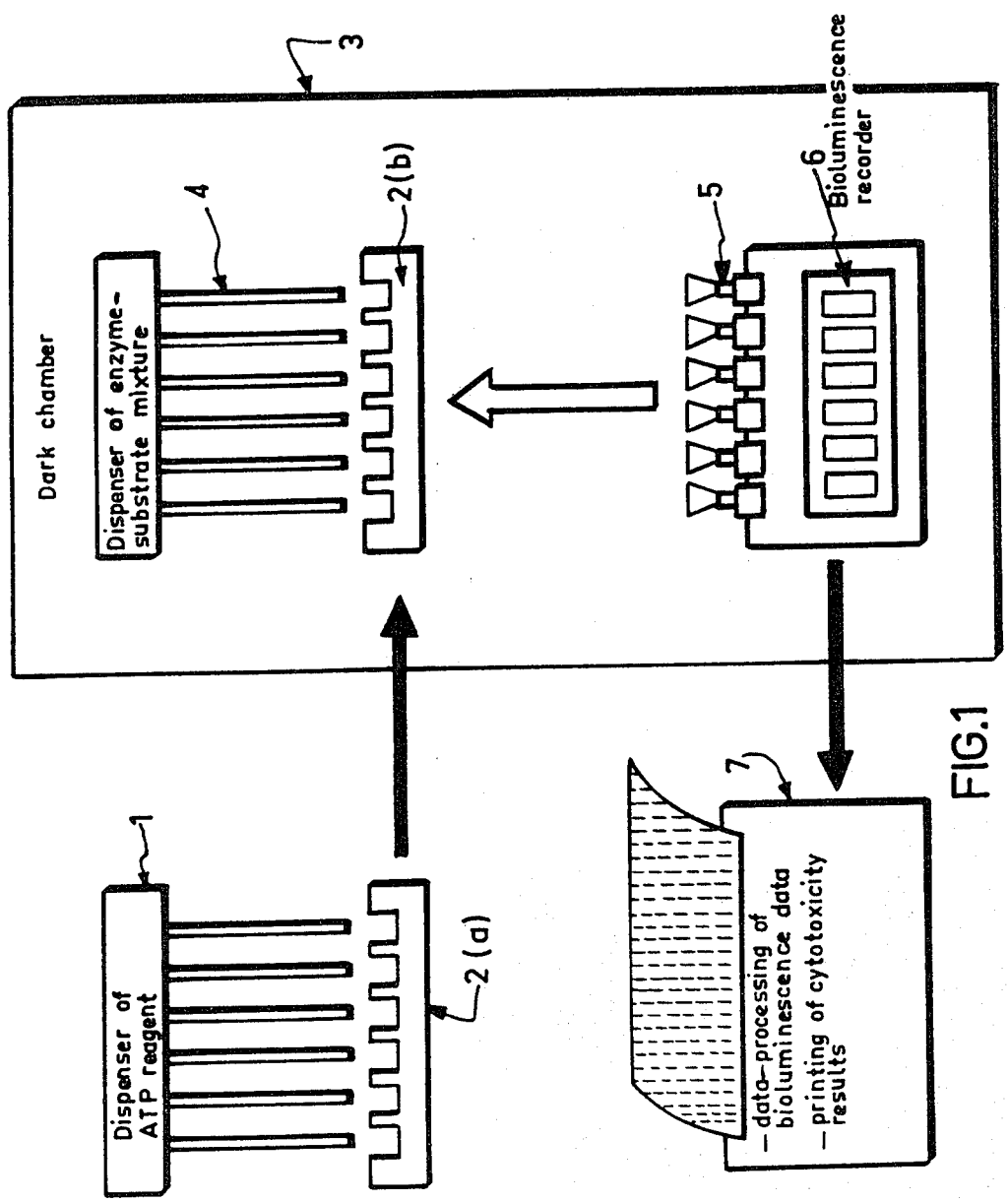
FIG. 1 is a schematic representation of the device of the invention.

This preferred embodiment will be now described in reference with the FIG. 1 which is a schematical representation of the device of the invention, appropriate for ATP determination.

The device of the invention represented on FIG. 1 comprises a reagent dispenser 1, for dispensing reagent into a container 2, wherein are the target cells, the serum and the complement. This container may be for example a microtiterplate or any other appropriate container. The device of the invention also comprises a dark chamber 3 wherein there is an enzyme-substrate dispenser 4, appropriate means for supporting the container 2 in an appropriate position under dispenser 4, light collector 5 and a bioluminescence recorder 6. The device of the invention is also provided with means 7 for data-processing the bioluminescence data and directly printing the cytotoxicity results, expressed as for example HLA typing or anti-HLA antibody specificity. The device of the invention also comprises means for transferring the container 2 from position (a) into position (b) and means for putting the container 2 off the dark chamber 3. All the means of the invention process are automatic.

The step (1) consists in extracting ATP from the cells by means of adding an appropriate reagent to the cell, serum and complement mixture.

In the invention process, a special nucleotide reagent for somatic cells is used. As a matter of fact, extraction of ATP from both microbial and somatic cells can be easily accomplished by a great variety of reagents. It will be easy to one skilled in the art to choose any appropriate reagent for extracting ATP from target cells.

This step can be easily automatised, as shown in FIG. 1 by using a reagent dispenser similar to the automatic dispensers already used for distributing cells, sera and complement.

The next step (2) consists in the ATP determination itself by using the firefly bioluminescent reaction which is now considered as the most sensitive analytical method for measuring ATP (Photochemistry 1969,10:153).

Briefly, the reaction involves an oxidative enzyme, the luciferase, and a light-producing substrate, the luciferin, in the following biochemical sequence:

Luciferase + Luciferin + ATP $\xrightarrow{Mg^{++}}$ Luciferase Luciferin

AMP + pyrophosphate

Luciferase Luciferin AMP→$O_2$ Oxyluciferin + AMP + $CO_2$ + hv (λ562 nm)

In optimal conditions, i.e. with a purified luciferin-luciferase preparation, at pH 7.75 and at 20° to 25° C., the reaction is specific for ATP.

According to this embodiment of the invention process, the luciferin-luciferase mixture is added in the dark to the preparation immediately after having extracted ATP. Then bioluminescence is immediately after measured in a photometer and light intensity emitted is expressed as an integrate value over a 10 second preset time. Results are given as integrated digital relative light units (RLU) and registered with a recorder 6 such, as for example a Hewlett Packard 97S. RLU can be transformed into equivalent ATP concentrations by internal standardization. Briefly, a sample is measured both before (A) and after (B) the addition of a known amount of ATP (cristalline ATP solution, 2 μg/ml, Lumac). An equivalence coefficient (k) between RLU readings and ATP concentration can thus be expressed:

$$k = \frac{\text{amount of ATP added}}{RLU(A) - RLU(B)}$$

and the concentration of ATP in a given sample (X) determined as follows:

$$ATP(X) = kx\ RLU(X)$$

However, since an extremely close correlation was found between ATP concentrations and corresponding RLUs, this expression of results did not appear necessary for comparison of experiments performed in the same technical conditions.

For example, in order to evaluate HLA antigens present on targets, ATP, found in the presence of HLA antisera, is always related to that found in the presence of control normal AB serum. The percentage of ATP loss is then evaluated as follows:

$$\% \text{ ATP loss} = \frac{\text{Mean ATP in target cells} - \text{Mean ATP in target cells}}{\text{Mean ATP in target cells with control serum.}}$$
with control serum        with test serum As for the preceeding steps and as shown on FIG. 1 this step of ATP determination can also easily be automatised. Using a dispenser (4), Luciferin-Luciferase mixture is automatically distributed and bioluminescence is measured by placing light collectors 5, such as micro diodes in series under the container 2(b), for example under the wells of the microtiter plate used as container 2; this arrangement allows simultaneous measurements of a complete row of the plate and by displacing the microtiter plate, reading is performed from one row to another in order to get over the whole plate. Lastly the processing module for data-processing should data-process the RLU values thus obtained for providing the cyto-toxicity results.

For example, when the invention process is used for HLA typing the processing module compares the RLU values of each well containing antiserum to the one containing normal AB serum and, by means of a simple programming, prints the HLA antigens beared by the cell to be typed. When the invention process is applied to the anti-HLA antibody detection, where the cells with known HLA antigen are used, the process module indicates the antibody specificity of the tested serum.

The process of the invention, based on the measurement of intracellular ATP content for evaluating and automatically quantifying cell lysis mediated by anti-HLA antibodies is a simple, rapid and reliable method.

It provides the same advantagesas the MCT i.e. it can be performed using 1 μl of antiserum, 500 lymphoid cells and 5 μl of complement using as container 2 the microtiter-plates usually used for HLA typing by MCT.

As MCT, it can be performed using stored microtiter plates (i.e. previously filled with antisera under oil), which appears important in view of its eventual use for routine HLA typing. Similarly, this process is of great interest for performing cross-match test between donor and recipient before transplantation. This test consists in detecting humoral antibodies in the recipient serum specifically directed against donor cells and is an imperative prerequisite before graft decision. Reproducibility of the method was excellent when routinely testing a series of subjects on different days (99.5%). The percentage of discrepancy in ATP measurements never exceeded 0.5% and appeared to be serum-dependent.

Furthermore, the ATP determination method of the invention as well as the device for carrying thereof may be applied to many other biological or industrial fields. For example, such method and device will appropriate and of a great benefit for large-scale determinations, for example of platelet aggregability or of presence of living germs in a great variety of materials, such as for example, urine, plasma, milk, vaccines, food products and similar products wherein the disturbing of such materials may be expressed by means ATP determinations.

Similarly the bioluminescence data are then data-processed by appropriate data-processing means for providing the disturbing of these materials.

The present invention will be further illustrated thereafter by the following examples wherein it is demonstrated that:

there exists a close correlation between tested ATP concentrations and bioluminescence intensity given in RLU values by a photometer.

ATP determination is appropriate for measuring CDC mediated by anti-HLA antibodies the process of invention is appropriate for HLA typing and a comparison with known methods is given.

EXAMPLE 1

Correlation Between Tested ATP Concentrations and Bioluminescence Intensity.

Increasing concentrations of a standard ATP solution were tested and the bioluminescence intensity was pointed out using the conventional luciferin-luciferase mixture and NRS as reagent.

Figure 2:
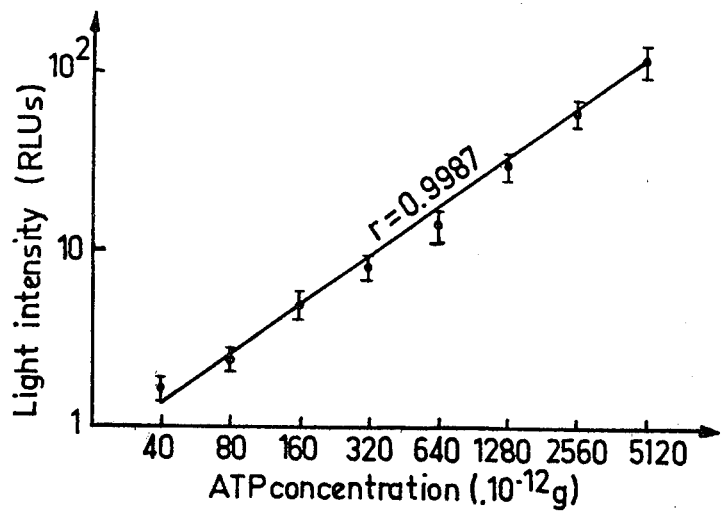

Diagram obtained is shown on FIG. 2.

Each points is the mean of 6 distinct measurements each of which is the mean of 3 samples. Calculation of the standard regression coefficient between light intensity and ATP concentration gave $r = 0.9987$ for 48 pairs corresponding to a p value $<0.001$. The same findings were obtained when ATP was determined after its extraction from human lymphoid cells.

Figure 3:
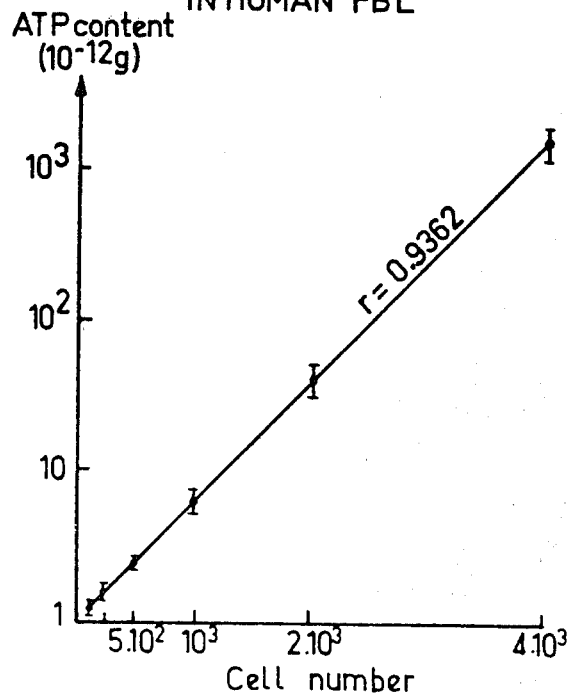

FIG. 3 is a diagramm wherein ATP content is expressed as a function of the cell number. Increasing numbers of cell (by a factor of 2) isolated from peripheral blood of one individual were tested on the same day. Each point is the means of 3 samples. Calculation of the standard regression coefficient between cell number and ATP number found after extraction by NRS gave $r = 0.9362$ for 18 pairs corresponding to p value of $<0,001$. This figure shows that there exists a close correlation between the number of cells and the amounts of ATP extracted by NRS. Consequently, it can be noted that ATP intracellular content can be precisely determined in as few as $5 \times 10^2$ cells.

EXAMPLE 2

ATP Determination for Measuring CDC Mediated by Anti HLA Antibodies A-Starting Materials

1. SERA

Normal control sera were obtained from AB never-transfused male volunteers.

Figures 4, 5:
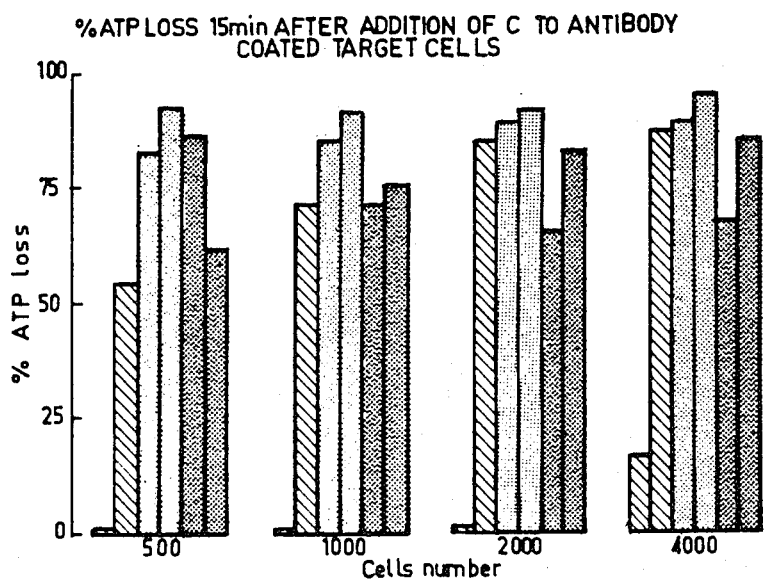

Sera from polytransfused patients were kindly provided by Mrs. L. Hallé (Dr. J. Y. Muller, CNTS, Paris) and constituted the HLA panel used in the experiments related in the present examples. Their HLA specificities are well defined since they routinely serve for HLA typing and their reactivity patterns are shown in FIG. 4.

2. CELLS

Lymphocytes were obtained from normal volunteers previously recruited to constitute an HLA panel. Their HLA phenotypes had been previously determined by tissue typing laboratories (Pr. J. Dousset, Hospital Saint-Louis, and Pr. J. P. Soulier, CNRS, Paris). Cells were isolated from heparinized blood according to the technique of Boyum [Scand. J. Clin. Lab. Invest. 21. Suppl. (1968), 97, 17] and were used either fresh or stored; details on procedures used for cell freezing and thawing are described in details elsewhere [Descamps B. 1978, p.25 in Thèse Doctorat d'Etat es-Science Paris]. Red phenol-free Hanks medium (Institut Pasteur) was used for resuspending cells ($5 \times 10^6$/ml or $5 \times 10^5$/ml).

3. COMPLEMENT

Sera from rabbits which had been previously individually screened for an absence of natural cytotoxins and titered in varying dilutions against antiserum with a known titer, were pooled and stored at $-80°$ C. in 1 ml aliquots. The same pool of sera was used as source of complement for all experiments reported herein.

4-REAGENT

"Nucleotide releasing reagent for somatic cells" (NRS) provided by LUMAC(Basel) was used as ATP-extracting reagent.

5. ENZYME-SUBSTRATE MIXTURE

Luciferin-luciferase purified reagent of Lumit (LUMAC Basel) was used.

Initial experiments designed to set up the invention process were performed using $8 \times 12$ well microtiter plates (Greiner) with a well capacity of 250 μl [macro-CDC-method] while final experiments for determining CDC mediated by anti-HLA antibodies were performed with Terasaki $6 \times 10$ microtiter plates (Falcon) having a much smaller well capacity of 15 μl [micro-CDC-method]. "CDC" means complement dependent cytotoxicity.

1. ATP macro-CDC method

Fifty μl of serum and 50 μl of the $5 \times 10^6$/ml cell suspension (i.e., $2.5 \times 10^5$ cells) were successively dispensed into each well and incubated at 37° C. for 15 minutes. Fifty μl of undiluted rabbit complement were then added to each well and the plate was again incubated at 37° C. for varying periods. The plates were centrifuged (400 g for 10 minutes) after the final incubation of cell with serum and complement. Supernatant was gently removed by aspiration and replaced by 100 μl of NRS. Immediately thereafter, the well content was homogenized by repetitive pipetting and rapidly transfered into a ($12 \times 47$ mm) glass counting tube. This latter was then immediately placed in the counting chamber of the photometer used for these experiments (Cell Tester M.1030, Lumac, Basel). In order to avoid the destruction of ATP, the time between addition of NRS to cell pellet and bioluminescence counting must be as short as possible.

2. Micro-CDC method

The procedure of the NIH microdroplet lymphocyte cytotoxicity test (MCT) recently revised by Terasaki et al [Terasaki et al 1978 Ann. J. Clin. Path.69 103] was used. Briefly, Terasaki plates (Greiner) previously filled with anti-HLA sera (1 μl per well) under mineral oil, were provided by Dr. J. Y. Muller (CNTS, Paris), patterns of serum distribution are shown on FIG. 4.

One μl of the $5 \times 10^5$ cell suspension was dispensed into each well using a Hamilton dispenser and plates were incubated at 37° C. for 15 min. Finally, 5 μl of rabbit complement were added to each well and plates incubated at 37° C. for 30 minutes. In this method the plates were not centrifuged after the final incubation. Thus, the whole content of each well was transferred by micropipetting into a glass counting tube, previously filled with 100 microliters of NRS. The tube was then, as for the above described experiments, immediately placed in the counting chamber of the photometer. This photometer was a cell Counter, M 2080, (Lumac, Basel) differing from the cell tester by being 1000-fold more sensitive, i.e. able to detect as low as $10^{-15}$ M of ATP.

Both above mentioned photometers were provided with a pumping system which automatically dispensed 100 μl of luciferin-luciferase purified reagent of Lumit (Lumac) in the dark counting chamber, within the tube containing the sample, just prior to the measurement. Bioluminescence measurement was immediately effected and was expressed as an integrated value over a 10 seconds preset time as above explained.

For each experiment, the same sample was always tested in triplicate and results expressed as the mean ±SEM. Usually, SEM did not exceed 5% of the mean. Very rare experiments in which it was greater than this value were excluded.

RESULTS

Three distinct multispecific HLA antisera, known to react with at least 80% of the cells from hereinabove mentioned HLA panel, and eight sera showing restricted HLA specificities were tested against eight distinct target cells. These cells were selected from the above mentioned panel for bearing HLA antigenic specificities reacting with the sera. The ATP macro-CDC technique above described was used, and a 45 min incubation time between serum-coated target cells and rabbit complement was observed. The experiment was repeated three times, using the same pattern for distributing cells and sera. Results of a typical experiment are shown on FIG. 4, wherein ATP loss (expressed in %) in human PBL observed after CDC mediated by anti-HLA antibodies. Shaded areas indicate expected positive reactions; in each of these cases but one (where ATP loss was 29%) positive reactions were observed, as defined by ATP loss$\geq$30%. Clear areas indicate expected negative reactions; in all but two of these cases (indicated by asterisks) ATP loss was either nil or well below 30%. These are results obtained from a typical experiment. They were found reproducibly in three experiments.

As shown on this FIG. 4 the ATP intracellular content was extremely reduced when target cells were incubated with multispecific HLA antisera. The percentage of ATP loss exceeded 80% almost in all antiserum-target combinations. When antisera with restricted HLA specificities reacted with target cells bearing corresponding HLA antigens, a similar, although less pronounced loss otvATP was found. Twenty-two reactions were part of this group. In 18 intracellular ATP loss exceeded 50%; it ranged from 29 to 35% in the 4 others. In view of these results, a 30% ATP loss was considered as being significant for considering cytolysis to be positive.

The third and last group of reactions in this experiment involved serum target combinations where no correspondence existed between respective HLA specificities. Forty-one distinct reactions were part of this group. No significant changes in ATP intracellular levels could be detected, except in two reactions where a marked loss of intracellular ATP content was observed (46% and 66% respectively). These two "extra positive" reactions were consistently found in all 3 experiments performed under the same pattern. They could not be explained by cross-reacting specificities between cells and sera.

Excluding these two observations, results from this series of experiments indicate that loss of ATP from human lymphoid cells is a suitable indicator for measuring cytolysis induced by anti-HLA antibodies.

The above experiments were carried out with the conventional materials for MCT, but by using the device of the invention the transfer of the content of each well by micropipetting into a glass counting tube is avoided since the reagent for extracting ATP is dispensed into each well of the microplate and said microplate is thereafter transferred into the dark chamber.

EXAMPLE 3

Comparison Between Intracellular ATP and $^{51}Cr$ Release for Detecting Anti-HLA Antibody Induced CDC Three multispecific HLA antisera from individual named DIE . . . JAR . . . CLO . . . ) were tested at various dilutions for their CDC activity against one target cell HLA type from the above mentioned panel. Serum DIE . . . was known to contain no antibodies against this target, as verified by standard MCT technique, whereas the two others were positive against this target cell.

Measurement of CDC by ATP loss (%) or $^{51}Cr$ release (cytotoxic index) from target cells and at various incubation times (from 15 to 90 minutes) after addition of complement showed similar results: DIE . . . was negative irrespective of incubation time with both techniques. Both JAR . . . and CLO . . . were positive at the first incubation time measured (15 min) and titrated identically. The results are gathered in table I.

As shown on this table, a close correlation between both assays was found: the two positive sera showing identical titer ($10^{-2}$) and being positive as soon as 15 min in both assays. However, ATP loss was already maximal at this first incubation time, whereas $^{51}Ca$ cytotoxic index further increased thereafter, reaching its maximum at 45 min. It was also verified in another experiments that reduction of intracellular ATP content could be detected as early as 5 minutes after adding complement to anti-HLA serum-coated target cells.

In FIG. 5 the % ATP loss obtained with a 15 minutes incubation time is indicated as a function of the cell number for the three above HLA antisera against two distinct HLA type target cells.

For each serum, the left column corresponds to one HLA type target and the right column to the other. All sera were tested undiluted and showed positive CDC against both targets, except serum DIE . . . , which was negative against one of the two targets. Increasing cell number did not modify the sera reactivity pattern.

EXAMPLE 4

ATP Determination for Typing HLA and B-Antigens

A-As it was already shown in example 1 (FIG. 3) the intracellular ATP content of human lymphoid cells can be evaluated in as few as 500 cells, provided that an ultrasensitive photometer (Luma-counter M 2080) is used.

The micro ATP CDC technique was performed using the same HLA antisera, and the same target cell as those used in the previous experiments reported in example 2. Sera were used undiluted and incubated for 15 minutes with increasing numbers of target cells (from 500 to 4000). Lastly, a 15 minutes incubation time was observed after addition of complement to serum-coated target cells. As shown on FIG. 5, CDC was easily measured with as few as 500 target cells and sensitivity of the assay did not increase when the number of cells was increased.

B-HLA typing microtiter plates, previously filled with anti-HLA sera under oil, according to the pattern shown on FIG. 6 were used. For each individual $5.10^2$ to $10^3$ lymphocytes were distributed into each well and plates were prepared in triplicate. The HLA typing was effectued according to the invention process following the different steps disclosed in the above example 1 with regard to microcytoxicity test.

The results are indicated in FIG. 6 in ATP loss %.

Reproducibility among the reactions observed in the three plates was found excellent. The percentage discrepancies between the sixty reactions measured in each plate were below 1%. Similarly, excellent reproducibility was observed when repeating tests on different days.

C-COMPARISON WITH MCT

Six distinct individuals were tested by both ATP and MCT assays. MCT assay was carried out according to TERASAKI et al.

Six distinct individuals were tested by both ATP and MCT CDC assays. FIG. 6 shows typical results obtained when typing one individual. Percentages indicate the % ATP loss calculated when comparing ATP intracellular content in the presence of anti-HLA serum to that in the presence of AB serum, and represent the mean value of % ATP loss in the corresponding wells from the three plates. Results of typing by MCT are indicated by positive or negative symbols. As shown on this figure, most of the reactions were concordant with the two assays and only 3 discordant reactions were observed.

Figure 7:
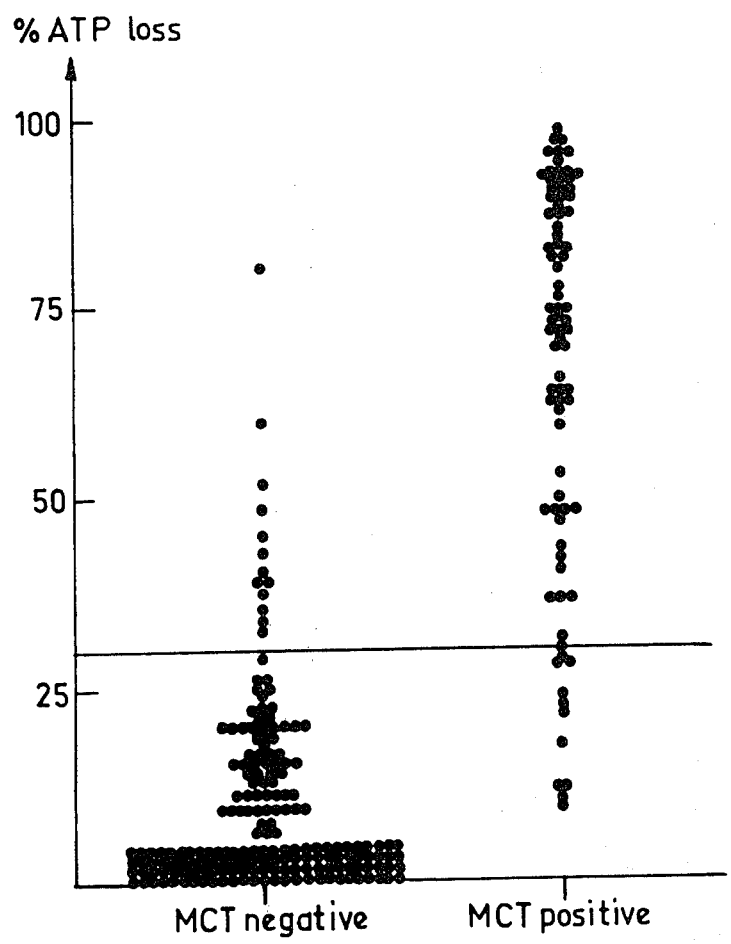

Further comparative experiments were carried out between ATP assay and MCT assay. 270 antiserum target cell reactions tested on the same day by both assays were compared. As shown on FIG. 7, 246 reactions (91%) were found concordant. The 24 discordant reactions included 13 ATP-positive/MCT negative reactions (5%) and 11 ATP negative/MCT positive reactions (4%).

TABLE I

CDC mediated by three HLA antisera at various serum dilutions and measured by percentage of ATP loss or $^{51}$Cr cytotoxic index (%)

| CDC measured by (min) | Serum dilution | | | | | | | | | | | |
|---|---|---|---|---|---|---|---|---|---|---|---|---|
| | $10^{-1}$ | | | $10^{-1}$ | | | $10^{-1}$ | | | $10^{-1}$ | | |
| | DIE | JAR | CLO | DIE | JAR | CLO | DIE | JAR | CLO | DIE | JAR | CLO |
| % ATP loss after incubation time of | | | | | | | | | | | | |
| 15 | 19 | 81 | 74 | 15 | 50 | 45 | 0 | 0 | 25 | 0 | 0 | 0 |
| 45 | 17 | 80 | 89 | 0 | 60 | 35 | 2 | 7 | 0 | 5 | 0 | 1 |
| 90 | 18 | 75 | 80 | 4 | 55 | 45 | 5 | 4 | 3 | 7 | 2 | 2 |
| $^{51}$Cr cytotoxic index after incubation time of | | | | | | | | | | | | |
| 15 | 12 | 59 | 55 | 10 | 45 | 17 | 3 | 5 | 4 | 0 | 2 | 8 |
| 45 | 10 | 75 | 75 | 7 | 55 | 25 | 0 | 10 | 0 | 1 | 5 | 4 |
| 90 | 11 | 80 | 80 | 12 | 60 | 30 | 0 | 7 | 1 | 3 | 7 | 2 |

What I claim is:

1. A process for determining the complement-dependent cytotoxicity mediated by anti-HLA antibodies contained in a test serum comprising:
combining target cells and test serum under conditions resulting in anti-HLA-coated target cells,
adding complement to the combined cells and serum,
incubating under conditions suitable for demonstrating cytotoxicity,
measuring the ATP loss from the target cells, and
comparing the measured value with a standard.

2. The process of claim 1, wherein the ATP measurement is carried out by bioluminescence.

3. The process of claim 1, wherein the ATP measurement comprises the steps of:
(1) extracting ATP by an appropriate reagent,
(2) adding an enzyme-substrate mixture specific to ATP
(3) measuring the bioluminescence.

4. The process of claim 3, wherein the enzyme substrate mixture is luciferin-luciferase mixture.

5. The process of claim 3, wherein the bioluminescence data are introduced into a computer and processed for determination of the cytotoxicity results according to the distribution pattern of cells and sera.

6. The process of claim 5, wherein the cytotoxicity results express the HLA specificity of antigens born by the cells to be typed.

7. The process of claim 5, wherein the cytotoxicity results are expressed as the HLA specificity of the antibodies present in the serum to be typed.

* * * * *